United States Patent [19]

Rhodes et al.

[11] Patent Number: 4,687,667
[45] Date of Patent: Aug. 18, 1987

[54] METHOD OF TREATING FUNCTIONAL BOWEL DISORDERS BY THE ADMINISTRATION OF PEPPERMINT OIL TO THE INTESTIVE

[75] Inventors: John Rhodes, Cardiff; Brian K. Evans, South Glamorgan, both of United Kingdom

[73] Assignee: J. B. Tillott Limited, London, United Kingdom

[21] Appl. No.: 461,011

[22] Filed: Jan. 26, 1983

Related U.S. Application Data

[63] Continuation of Ser. No. 182,583, Aug. 29, 1980, abandoned, which is a continuation of Ser. No. 20,049, Mar. 13, 1979, abandoned.

[51] Int. Cl.$^4$ ............................................. A61K 35/78
[52] U.S. Cl. ................................................. 424/195.1
[58] Field of Search ........................................ 424/195

[56] References Cited

U.S. PATENT DOCUMENTS 3,855,406 12/1974 Adams et al. ........................... 424/35
3,927,195 12/1975 Messora .................................. 424/35
3,957,999 5/1976 Sharpe .................................... 424/270

FOREIGN PATENT DOCUMENTS 2207705 1/1972 France .

OTHER PUBLICATIONS

Ellingwood–*Materia Medica and Therapeutics*, Sixth ed., Pub. by The Ellingwood's Therapeutist Co., 1907, pp. 339–341.
Husa's–*Pharmaceutical Dispensing*, Mack Pub. Co., Sixth Ed., 1966, pp. 136–143 & 158.

*Primary Examiner*—Frederick E. Waddell
*Attorney, Agent, or Firm*—Nixon & Vanderhye

[57] ABSTRACT

Essential Oils (including Arematic Carminatives) and their active components are selectively administered to the intestine to treat irritable colon syndron and other intestinal disorders responsive to treatment with a carminative. The oils are presented in a rectal or, preferably, enteric preparation, especially an enterically coated hard gelatine capsule. Peppermint oil is presently preferred.

4 Claims, No Drawings

METHOD OF TREATING FUNCTIONAL BOWEL DISORDERS BY THE ADMINISTRATION OF PEPPERMINT OIL TO THE INTESTIVE

This is a continuation of application Ser. No. 182,583, filed Aug. 29, 1980, now abandoned, which is a continuation of Ser. No. 020,049, filed Mar. 13, 1979, now abandoned.

The present invention relates to carminative preparations containing carminative essential oils (as hereinafter defined) or active components of such oils. It provides novel preparations for selectively administering a carminative in the intestine.

Functional bowel disorders characterised by recurrent intestinal distension, colicky pain, and intermittent change in bowel habit are common. They are frequently described as "irritable colon syndrome", which is a diagnosis arrive at after exclusion of other organic pathologies. This group of conditions may not be a single group with a simple basis of one one aetiological factor but it is probably the most common single clinical problem relating to disorders of the large bowel. The condition tends to be chronic, with relapses even after a time of normal health.

Irritable colon syndrome and certain other intestinal disorders such as diverticular disease and apastic colon could be relieved by administering to the intestine a muscle relaxant and/or antispasmodic drug. However, no wholly satisfactory treatment of these disorders has been available. It is therefore an object of the present invention to provide a relatively inexpensive, easily administered and effective treatment for these disorders.

Essential oils (otherwise known as aetherolea) are ethereal oils obtained from plants and some of these oils have been known as medicaments since the very beginning of pharmacy. Many belong to the terpene group whilst others are related to benzene derivatives. They exert a mild irritant action on the mucous membranes of the mouth and digestive tract and are mild expectorants. In particular, they are used as carminatives (i.e. muscle relaxant with antispasmodic effect) after meals and for the relief of gastric discomfort and of flatulent colic and also to counteract the griping action of purgatives (see "The Extra Pharmacopoeia," 27th Edition, Martindale). Aromatic carminatives are volatile substances related to essential oils and having similar carminative action and a clear distinction between aromatic carminatives and essential oils is not always drawn.

Accordingly, the term "essential oil" as used in this Specification includes aromatic carminatives unless the context clearly implies otherwise. The term "carminative essential oil" is used to mean those essential oils and aromatic carminatives which are sufficiently non-toxic and otherwise pharmacologically acceptable for gastrointestinal use and thereby to exclude such toxic essential oils as pine and turpentine.

A substantially complete list of essential oils is given at pages 1011 to 1023 of "The Extra Pharmacopoeia", Edition 27, Martindale.

When administered for their known carminative effect, the essential oils are taken orally in a form which is effective in the stomach. The dose administered is limited by the irritant action of the essential oils on the mucous membranes and particularly by action on the gastro-oesophageal spincter. Thus, the essential oil so administered passes into the small intestine, and eventually into the colon; the amount is insufficient to produce any substantial carminative effect in the intestine and certainly insufficient for the effective treatment of irritable colon syndrome, diverticular disease or spastic colon. To the best of our knowledge the possibility of using essential oils for treating of such intestinal disorders has been dismissed, perhaps subconsciously, because of the dose limitations imposed by the effect on the mucous membranes of the oesophagus and stomach and/or gastrooesophageal spincter. The fact of the matter is that our investigations indicate that, despite the long known carminative action of essential oils and the long felt need for a readily administered and effective treatment for irritable colon syndrome, there has been no previous proposal to use essential oils for inducing a carminative effect in the intestine.

It is an object of this invention to provide a preparation which is readily administered and effective for the treatment of irritable colon syndrome and other intestinal disorders responsive to treatment with a carminative.

We have found that carminative essential oils provide a readily administered and effective treatment for irritable colon syndrome when presented as an enteric preparation or as a rectal preparation. By "enteric preparation", we mean a preparation which when taken orally will pass through the stomach substantially without release of the active principle but which will release the active principle in the intestine. By "rectal preparation", we mean a preparation which is specifically formulated for rectal administration and exclude any preparations suitable for oral administration. Enteric preparations and rectal preparations are well known per se and accordingly it should be clearly understood that the invention resides in the presentation of carminative essential oils in such preparations as distinct from enteric or rectal preparations in general.

The present invention provides in one aspect thereof an enteric preparation (as hereinbefore defined) containing as a pharmacologically active ingredient a carminative essential oil (as hereinbefore defined) or a carminative component thereof.

In a second aspect, the invention provides a rectal preparation (as hereinbefore defined) containing as a pharmacologically active ingredient a carminative essential oil (as hereinbefore defined) or a carminative component thereof.

The essential oil or component thereof can be obtained by extraction from a plant or can be synthetically produced. The presently preferred carminatives are those containing methanol, particularly those obtained from species of Mentha especially peppermint oil (B.P.). Peppermint oil (B.P.) contains 4 to 10% w/w esters calculated as menthyl acetate, not less than 44% w/w free alchols calculated as menthol and 15 to 32% w/s ketonic compounds calculated as menthone. It is a colourless, pale yellow or greenish-yellow liquid obtained by distillation and, if necessary, subsequent rectification from the fresh flowering tops of the plant *Menthax piperita* (Labiatae). Non-limiting examples of other carminative essential oils and carminative components thereof are benzaldehyde, camphor, carvone, cineole, cinnamaldehyde, cinnamon, citral, clove, eucalyptus, eugenol, linalol, menthol and thymel.

It is preferred that the composition is an enteric preparation, especially a capsule coated with an enteric coating. Enteric coatings are widely used in the pharmaceutical industry and are formed of substances which are relatively insoluble in the acid medium of the stomach but disintegrate in the medium of the small intestine. The capsule suitably is a hard gelatin capsule and a suitable enteric coating is a cellulose acetate phthalate coating. Other suitable coatings include enteric coating lacquers based on polymeric methacrylates. Other enteric preparations can be used, such as enterically coated tablets containing the carminative substance in a microencapsulated form or loaded on a suitable excipient.

As mentioned previously, the preparation of the invention can be a rectal preparation. Examples of such preparations are enemas and, preferably suppositories. Suitably, the suppositories can be in the form of soft gelatin capsules enclosing the carminative substance.

Usually the carminative will be administered in a daily dose of 0.15 ml to 3.0 ml, especially 0.6 ml to 2.4 ml and particularly about 1.2 ml. The actual dose will vary from patient to patient depending inter alia on the identity of the carminative, patient body weight, tolerance to the carminative and nature and degree of disorder being treated. It is convenient for each unit dose to contain 0.05 ml to 0.5 ml, especially 0.15 ml to 0.35 ml and particularly 0.2 ml to 0.3 ml of the carminative. By unit dose we mean that dose which is adapted or intended to be administered to the patient as a single unit, although several single units may be administered at the same time. Usually, the unit dose will be a discrete entity but this is not necessarily so, as in the case of an enema where sufficient preparation for several enemas may be provided in the same container (i.e. the container contains several unit doses) to be measured out as required.

The following is a description, by way of example only, of a presently preferred embodiment of the invention.

EXAMPLE

Self-locking hard gelatine capsules (size 2; 0.37 ml) available under the Trade Mark LOK-CAPS were each loaded manually with 0.15 ml Peppermint Oil B.P. dispensed from an automatic pipetting syringe. The filled capsules were placed in a coating tower where they were carried in a heated (55° C.) air stream whilst being sprayed with an enteric coating solution. The coating solution had the following composition by weight:
cellulose acetate phthalate: 3%
diethyl phthalate: 1%
silicone fluid (200 c.s.): 1%
ethyl acetate: 30%
acetone: to 100%
Density of solution: 870 mg/ml
Solids content: 5.5%

An amount of 43.01 ml per 100 capsules was employed to provide a theoretical coating of 6 mg/cm$^2$, which is an excess of that theoretically required in order to allow for losses during the coating process.

It will be appreciated that the process described above is a small scale process devised for the purposes of preparing several hundred capsules for clinical evaluation. Production scale processes will almost certainly differ both in terms of the procedure employed and the relative proportions of the coating composition.

Enteric-coated capsules obtained as described above were subjected to the B.P. 1973 disintegration test for enteric-coated tablets (see pages A123 British Pharmacopoeia 1973). The capsules were immersed in 0.06N Hydrochloric acid for a 3 hour period and during that time no distintegration took place. However, all the capsules disintegrated within 60 mins. When immersed in a standard solution of pH 6.8.

In order to evaluate in vivo disintegration, enterically-coated capsules were prepared as described above but filled with (a) a barium sulphate composition or (b) iodised poppy-seed oil. Each of twelve patients chosen at random from patients attending a Barium Meal Clinic were given two of the barium sulphate capsules and two of the iodised poppy-seed oil capsules. The patients were subsequently examined radiologically. The average dissolution time was 143 minutes and the site of dissolution was in the region of the small bowel. The results indicate that the capsules pass intact through the stomach and greater part of the duodenum. Disintegration commenced at the distal end of the duodenum, continuing into the jejunum and finally the capsule releases its contents along the length of the ileum.

Thirty-two patients attending a Colon Clinic showing symptoms consistent with irritable colon syndrome were admitted voluntarily to an open clinical trial. The dose employed was one enteric-coated peppermint oil capsule (prepared as described above and containing 0.15 ml Peppermint Oil B.P.) taken three times a day before meals. Clinical assessment of each patient was carried out after an initial treatment period of 14 days. If no side-effects were evident after this period and the patient had benefited from the treatment, it was continued for a further 14 days. After the second 14 day period, the overall patient response to the treatment was documented and a comparison made with previous therapy. The treatment was continued indefinitely if beneficial.

Thirteen patients showed excellent response and another twelve showed good response; the remaining seven did not find the treatment beneficial.

Only one patient showed any signs of toxic effects and this took the form of a hypersensitivity reaction to the menthol content of the oil, which reaction disappeared upon terminating the treatment. One other patient suffering from achlorhydria complained of heartburn and burping caused as a result of the capsules disintegrating in the abnormally high pH of the achlorhydric stomach. Some patients who found the treatment beneficial had previously been prescribed diphenoxylate, papverine, dicyclomine or mebeverine without success.

The results of the test indicated that peppermint oil in enterically coated hard gelatine capsules is an acceptable and effective treatment of irritable colon syndrome.

We claim:
1. A method of treating irritable colon syndrome in humans which comprises administering selectively to the intestine of a human with irritable colon syndrome 0.05 to 3.0 ml of peppermint oil as an enteric preparation or rectal suppository.
2. The method of claim 1, wherein 0.15 to 3.0 ml of peppermint oil is administered daily.
3. The method of claim 1, wherein 0.6 to 2.4 ml of peppermint oil is administered daily.
4. The method of claim 1, wherein about 1.2 ml of peppermint oil is administered daily.

* * * * *